United States Patent
Farkas et al.

(10) Patent No.: US 10,067,062 B2
(45) Date of Patent: Sep. 4, 2018

(54) APPARATUS AND METHOD FOR CONTROLLING AN ATOMIC EMISSION SPECTROMETER

(71) Applicant: Thermo Fisher Scientific (Ecublens) SARL, Ecublens (CH)

(72) Inventors: Romain Farkas, Lausanne (FR); Tony Maulaz, Champagne (CH)

(73) Assignee: Thermo Fisher Scientific (Ecublens) SARL, Ecublens (CH)

( * ) Notice: Subject to any disclaimer, the term of this patent is extended or adjusted under 35 U.S.C. 154(b) by 0 days.

(21) Appl. No.: 15/524,915

(22) PCT Filed: Nov. 6, 2015

(86) PCT No.: PCT/EP2015/075908
§ 371 (c)(1),
(2) Date: May 5, 2017

(87) PCT Pub. No.: WO2016/071493
PCT Pub. Date: May 12, 2016

(65) Prior Publication Data
US 2017/0322161 A1    Nov. 9, 2017

(30) Foreign Application Priority Data

Nov. 7, 2014    (GB) .................................. 1419888.1

(51) Int. Cl.
*G01J 3/30* (2006.01)
*G01N 21/67* (2006.01)
(Continued)

(52) U.S. Cl.
CPC .............. *G01N 21/67* (2013.01); *G01J 3/443* (2013.01); *G01N 27/04* (2013.01)

(58) Field of Classification Search
CPC ........ G01N 21/67; G01N 21/71; G01N 21/72; G01N 21/31; G01N 21/04; G01N 1/22; G01N 30/68; G01J 3/02; G01J 3/44
See application file for complete search history.

(56) References Cited

U.S. PATENT DOCUMENTS

| 4,111,556 A | 9/1978 | Grisar et al. |
| 2009/0079980 A1 | 3/2009 | Goulter et al. |

(Continued)

FOREIGN PATENT DOCUMENTS

| DE | 102005057919 A1 | 6/2007 |
| JP | 2006308524 A | 11/2006 |

*Primary Examiner* — Abdullahi Nur
(74) *Attorney, Agent, or Firm* — Denton W. McAlister (57) ABSTRACT

A controller (316) and method for establishing safe operation of an atomic emission spectrometer (AES) to analyze a sample (100) arranged on a sample holder (102) of the AES. The controller (316) is configured to receive a measurement of at least one test parameter indicative of the arrangement of the sample (100) on the sample holder (102). The at least one test parameter is then compared to a range of target values for that test parameter to determine if the sample (100) is arranged correctly on the sample holder (102). The test parameters may include an electrical parameter dependant on a current between a first and a second terminal at the sample holder (102), gas pressure in a gas chamber housing an electrode of the AES, or displacement of a portion of the sample holder.

32 Claims, 6 Drawing Sheets

(51) Int. Cl.
*G01J 3/443* (2006.01)
*G01N 27/04* (2006.01)

(56) References Cited

U.S. PATENT DOCUMENTS

| | | | |
|---|---|---|---|
| 2010/0069731 A1* | 3/2010 | Harra | A61B 5/05 600/365 |
| 2013/0030717 A1 | 1/2013 | Halderman et al. | |

* cited by examiner

APPARATUS AND METHOD FOR CONTROLLING AN ATOMIC EMISSION SPECTROMETER

FIELD OF THE INVENTION

This invention relates to the field of controllers for a spark or atomic emission spectrometer (AES), particularly for controllers of a spark generator. Specifically, the invention is concerned with establishing safe operation of an AES.

BACKGROUND

Spark or atomic emission spectrometry, also known as optical emission spectroscopy, is a well-known technique for analysis of samples. A solid sample is subjected to a spark or electrical discharge which vaporises a portion of the sample and promotes atoms and ions into excited states. Light is emitted during relaxation of the excited atoms and ions into lower energy states, with subsequent spectroscopic analysis of the discharged light providing information on the material composition of the sample.

Spark or arc atomic emission spectrometers (AES) commonly comprise a spark stand (or spark table) having a sample holder consisting of a receiver plate or analysis table for mounting the sample. The receiver plate can be grounded or held at a fixed voltage and contains an aperture to a gas chamber below. The sample, which is larger than the aperture, can be mounted over the aperture to form a gas-tight seal between the sample and the receiver plate. Preferably, a clamp is used to hold the sample firmly in place over the aperture and secure the sample to the receiver plate. An electrode of the AES is arranged in the gas chamber proximate to but spaced apart from the aperture of the plate. Applying a voltage to the electrode ignites a spark or arc between the electrode and plate or sample. This causes a portion of the sample which is exposed to the spark through the aperture of the plate to be vaporised or ablated.

To avoid adulteration of the optical spectra, the sample is vaporised and excited in the presence of an inert gas such as argon. Typically, a flow of the inert gas is passed through the gas chamber which houses the electrode and in which the spark occurs. When the sample is correctly mounted on the receiver plate so as to form a gas-tight seal, air cannot enter the gas chamber or argon gas leak from the gas chamber. However, if the sample is mounted incorrectly, even small amounts of air leaking into the gas chamber can lead to anomalous spectra and so inaccurate analysis of the sample.

When the sample is correctly arranged on the receiver plate, the clamp typically provides a downward pressure to form the gas-tight seal between the sample and the receiver plate. However, if the sample is not correctly seated, the clamp can connect to the sample at an angle. This risks a poor seal being formed between the sample and the receiver plate. Moreover, the sample can sometimes be displaced during set-up or use of the AES, for example due to contact with the operator or because the sample is poorly secured to the sample holder and moves due to pressure exerted from the gas chamber below. This can cause the seal between the plate and sample to leak, thereby disrupting the sample analysis and potentially exposing the electrode to the operator.

Spark generators for generating the spark or arc provide a spark having a specific waveform profile for providing superior vaporisation and excitation of a sample. To generate the spark or arc, spark generators often use a combination of a high-current-controlled source and a high-voltage power supply. Each spark is a combination of a high-voltage discharge between the electrode and the sample and amplitude modulated current arranged to flow through the electrode, to the sample and the sample holder. When the sample is incorrectly located on the receiver plate, the spark can fail to ignite, despite a high voltage being present at the electrode. Not only can this causes errors or anomalies in any sample analysis, but also results in an inherent risk to the user due the hazardously high voltage levels created by the apparatus. Even if the spark is ignited, improper location of the device or faults within the device can result in serious electrical shocks or electrical burns to the operator.

DE 10 2005 057 919 provides an approach to trigger a safety shutdown of the AES in the event that the charge flowing through the electrode exceeds a threshold value during certain periods of the spark. In particular, the apparatus provides a number of arrangements of the circuitry of the spark generator to prevent an electric shock to the operator sufficient to be harmful to the human body. In one example, a small test voltage is applied between the electrode and the receiving area before initiating a spark. In this arrangement, if a voltage drop is observed between the electrode and the receiving area it is assumed that there is an unsafe connection, for example due to contact with the operator. As a consequence, the high-voltage power supply for energising the electrode is prevented from activation. Providing no current is passed between the electrode and the receiving area as a result of the test voltage, the apparatus is permitted to generate a spark.

Against this background, it is desirable to provide an apparatus and method that offers an improved arrangement for establishing safe operation of an atomic emission spectrometer (AES).

SUMMARY OF INVENTION

The present invention provides a method and controller for enhancing the safety of operation of a spark stand or spark table of an Atomic Emission Spectrometer (AES). For example, the present application provides a method to identify improper arrangement of the sample in the spark stand due to improper use or accidental misuse. The method may then implement a safe shutdown of the electrode within the AES or prevent the electrode from being energised. By providing a method to verify safe operation of the AES, the invention provides a reliable method to reduce the risk of electrical shock or associated electrical burns to the user of the AES due the hazardously high voltages applied within the apparatus.

Safe operation of the AES requires proper and correct use by the operator. In particular, risk in relation to operation of the AES is lessened where the sample is correctly arranged on the sample stand of the AES. Even though an operator may be properly trained, errors or accidental misuse may still occur. For example, the sample may not form a leak-proof seal with the sample receiver, or the sample may not be properly secured on the sample receiver. In this case, the sample may move when an overpressure of gas is generated in the gas chamber or when the arc is applied. If the sample moves out of position, there is a risk of exposure of the operator to the hazardously high voltages on the electrode.

Moreover, even in the event that the sample is correctly placed at the beginning of an analysis, it is not possible to exclude the possibility of accidental contact of the operator with the sample or spark stand. Once again, this can cause the sample to move and expose the operator to the risk of electrical shock. In addition to the safety risk to the operator, incorrect placement of the sample (or movement of the sample when the AES is in use) will cause problems and errors in any analysis of the sample.

The invention provides a method and apparatus for measuring various characteristics of the sample, so as to ascertain whether the sample is correctly positioned. The method and apparatus establish whether the sample is correctly positioned by comparison of the measured characteristics against preferred values or target values for each measured parameter. The target values represent the ideal results for the measurement if the sample is correctly arranged in the sample holder. If the measured characteristic values are not within the range of the target values, it is assumed that the sample is incorrectly arranged (or there is a fault within the equipment) and so commencement of the sample analysis is prevented, or a safety shut down of the apparatus is prompted.

In a first aspect of the invention, there is provided a controller for establishing safe operation of an atomic emission spectrometer (AES) to analyse a sample arranged on a sample holder of the AES, the controller configured to receive a measurement of at least one test parameter indicative of the arrangement of the sample on the sample holder. The controller is further configured to compare the at least one test parameter to a range of target values for the at least one test parameter to determine if the sample is arranged correctly on the sample holder. Advantageously, determining whether or not the sample is correctly positioned and secured on the sample holder provides a good indication whether the apparatus can be operated safely.

The test parameter may be any type of measurable parameter or characteristic that defines, indicates or is representative of the sample arrangement or how the sample is seated at the sample holder. The range of target values may represent the preferred value for the test parameter when the sample is correctly arranged. The range of target values may be predefined (and stored at the controller or over a network), or may be input by the user. The target values may vary for different configurations of the apparatus, and for different types of sample.

In some circumstances, the range of target values may be a range with a specific start and end value (for example, between X and Y). In other cases, the range of target values may refer to a lower or upper limit or threshold which needs to be met, exceeded or for the measured value to be below (for example, that the test parameter is less than Y, or greater than X).

Preferably, the controller is further configured to disable an electrode of the AES if the at least one test parameter is not within the range of target values. Disablement of the electrode may comprise putting the electrode in an unenergised state, setting the electrode or the electrode power supply to an off state, or disabling the electrode from being energised in any other way. Disabling of the electrode includes both prevention of a voltage being applied to the electrode, or removing or grounding any voltage that has already been applied. Disabling an electrode may be achieved by effecting a safety shut down of the electrode power supply, or the AES more generally. In particular, the controller regulates the operation of the electrode according to a determination of the safety of operation on the basis of objective measurements of the apparatus. As the controller automates this process, this reduces the likelihood of the operator mistakenly or inappropriately energising the electrode under unsafe conditions i.e. reduces human error.

The at least one test parameter may be an electrical parameter dependent on a current between a first and second terminal at the sample holder. Preferably, the electrical parameter may be measured after application of a low current between the first and second terminal. Specifically, the current applied has a magnitude such that the associated voltage would not be hazardous or harmful to an operator or other person making contact with the terminals. One of the first and second terminals may be held at a ground potential. The voltage between the two terminals as a result of the applied current can be measured. Therefore, as the injected current is a known quantity, a resistance or impedance between the terminals can be calculated. Alternatively, an electrical parameter could be measured after application of a small voltage between the first and second terminals.

The electrical parameter may be an impedance, Z, which can be calculated as the ratio of the voltage, U, to current, I. In other words, $Z=U/I$. Advantageously, the electrical impedance verifies that a sample is both present and appears to be correctly loaded at the sample holder. For example, if the analysis has been initiated before loading of the sample, no current will pass between the first and second terminals. If the sample is loaded but not properly secured to the sample holder, poor contact may be made between the sample and contact portions of the sample holder, thereby resulting in a much higher impedance that if the sample were correctly seated. The impedance may also indicate that a component is placed between the two terminal that should not be present (for example, a finger of the operator, or another item), as this may yield an impedance greater than expected for a genuine sample.

Optionally, the at least one test parameter may be a gas pressure measured in a gas chamber housing an electrode of the AES. The gas pressure may be an absolute gas pressure in the gas chamber at a particular time, or may be the difference in the gas pressure between a first time and a second time. The gas pressure provides an indication of whether a gas-tight seal has been formed between the sample and the sample receiver, such that the sample is correctly seated and covers the opening to the gas chamber. If the gas pressure is lower than the target values of the pressure, this indicates a leak from the gas chamber which may be caused if the sample is not appropriately secured.

As a further alternative, the at least one test parameter may be a displacement of a portion of the sample holder. Alternatively, the test parameter may be a measurement otherwise indicating a movement of the sample. Advantageously, this measurement parameter can be recorded and evaluated during the course of a sample analysis. Therefore, this measurement parameter can provide an indication if the arrangement of the sample in the sample holder has changed or moved during analysis (for example, due to the operator inadvertently making contact with the sample or spark stand). If the sample is indicated to have moved, a safety shutdown of the apparatus can be initiated.

Optionally, the controller is configured such that receiving the measurement of the at least one test parameter comprises receiving a measurement of each of two or more test parameters. Furthermore, the controller may be configured such that comparison of the at least one test parameter to a range of target values comprises comparison of each of the two or more test parameters to a range of target values for each test parameter. Any number of test parameters could be measured. Increasing the number of measured test parameters may increase the reliability and dependability of the determination of whether the sample is correctly mounted. In one example, a first and a second test parameter are measured and compared to a respective target range of values for each of those test parameters (i.e. the first test parameter is compared to a first set of target values, and the second test parameter is compared to a second set of target values). In another preferred example, three different test parameters are measured, and each of the three test parameters are compared to an associated range of target values for the particular test parameter.

Preferably, the controller is further configured to disable an electrode of the AES if one or more of the two or more test parameters are not within the range of target values for that test parameter. For example, the electrode can be disabled if any one of three measured test parameters do not fall within the expected target values. Disabling the electrode includes grounding or removing the voltage from the electrode, or preventing a voltage from being applied to the electrode. The controller can disable the electrode in the event that any one of the measured test parameters does not fall within the range of target values. Advantageously, this decreases the risk to the operator by providing additional checks and balances before the electrode can be energised. Alternatively, the electrode can be disabled if a predetermined number of the test parameters do not fall within the given range of target values.

Optionally, each of the two or more test parameters is any one or more selected from the group consisting of: an electrical parameter dependent on a current between a first and a second terminal at the sample holder; a gas pressure in a gas chamber housing an electrode of the AES; and a displacement of a portion of the sample holder. Beneficially, each test parameter assists to characterise the positioning and seating of the sample on the sample holder in a different way.

Preferably, the two or more test parameters are not the same test parameter. Advantageously, measuring a variety of test parameters gives a more complete characterisation of the sample arrangement.

At least one of the two test or more parameters may be the electrical parameter. The electrical parameter may be measured between a first and second terminal at the sample holder, wherein the sample (when set-up correctly) is placed between the two terminals to complete an electrical circuit. Measuring an electrical parameter in the electrical circuit (such as the current, voltage, impedance or resistance) provides a relatively simple verification both that the sample has been mounted, and that is securely and properly fastened in the sample holder. As the sample provides a connection between the two terminals, if the sample is not correctly arranged, there may be poor electrical contact between each terminal and the sample.

The first terminal for measurement of an electrical parameter may be at a sample receiver of the sample holder and the second terminal may be at a clamping element of the sample holder or the sample tip of the sample holder (or any element for securing the sample into position). The clamping element or sample tip may be used for securing or holding the sample to a sample receiver or analysis table of the sample holder. In a particular case, a current may be applied to the clamping element (second terminal) and the sample receiver (first terminal) may be referenced to a ground potential. The voltage between the first and second terminals can therefore be measured, and an electrical characteristic dependent on the applied current and measured voltage can be used as the test parameter.

The controller may be further configured to initiate a current between the first terminal and the second terminal. For example, the controller may control a power supply arranged to provide a low current to either the first or second terminal. In other words, the controller may supply a very low and controlled current (i.e. sufficiently low not to be hazardous to human health) to one of the terminals, which is a test current. In a particular example, the current is applied to the clamping element, and the sample receiver is grounded. After placing the sample between the clamping element and sample receiver, the voltage between the two elements of the sample holder can be measured. Even if the operator of the AES comes into contact with the two terminals whilst the test current is applied, the current is sufficient low that the operator would not be harmed.

Optionally, the electrical parameter is impedance. In a particular example, the target range of values for the impedance is between 0 and 100 mΩ, although this may vary for different sample holder configurations and different types of sample. Advantageously, the range of target values for the impedance will not include an impedance close to that of the human body.

Preferably, at least one of the two or more test parameters is the gas pressure. An overpressure or pressure greater than atmospheric pressure may be created in the gas chamber if the sample is correctly seated on the sample receiver. Therefore, preferably the target values for the gas pressure will be a pressure greater than atmospheric pressure. Beneficially, measurement of the gas pressure indicates if the gas chamber is leaking, for example as a result of a poor seal between the sample and the sample receiver.

Optionally, the gas pressure is measured after elapse of a time interval. In one example, it is expected that a pressure greater than the atmospheric pressure will be generated within a predetermined time following initiation of a gas flow through the gas chamber. Therefore, the gas pressure may be measured after the predetermined time interval, to establish whether a pressure greater than atmospheric pressure has been reached. If the gas chamber is leaking (for example, because the sample does not give a proper seal at the aperture in the sample receiver), the gas pressure will not reach the overpressure or required threshold pressure within the predefined time. As an alternative, a pressure change between a measurement at a first time and a measurement at a second time may be calculated.

At least one of the two or more test parameters may be the displacement. Measurement of this test parameter may be particularly useful to indicate whether the sample has moved during a sample analysis and whilst hazardously high voltages may be present at the electrode.

The displacement may be equal to a difference between a first position of a clamping element of the sample holder measured at a first time and a second position of the clamping element of the sample holder measured at a second time, the clamping element for securing the sample to the sample receiver. The second time may be later than the first time, following elapse of a time interval from the first time. For example, the second time may be a few milliseconds, 1 second, 3 seconds or much later than the first time. Preferably, the time interval may be very short so that the displacement is measured in "real-time". Advantageously, this allows a brief contact or impulse at the sample to be detected quickly after the event.

Preferably, the displacement is an angular displacement of the clamping element. Optionally, the angular displacement may be measured having units relating to the step of an encoder, or an angle (in degrees, radians or revolutions, for example). Alternatively, the displacement is the lateral displacement of a portion of the sample holder, or the sample itself. Beneficially, the angular displacement of the clamping element may provide a sensitive measurement to even a small movement of the sample.

Disabling the electrode may comprise controlling a switch to regulate a high-voltage current through the electrode. For example, the switch may be any type of circuit breaker, electrical conductor (for example to short-circuit a voltage to ground potential), or transistor.

Optionally, the controller is further configured to provide a visual indicator when the electrode is energised. One or more visual indicators may be illuminated to warn the user against the presence of hazardous voltages on the electrode, to indicate that the controller has determined the sample is correctly seated, or to indicate if analysis is underway. Advantageously, providing a visual indicator may further reduce risk to the operator.

The controller may receive instructions from a user or operator of the AES using a user interface or human-machine interface. For example, this may comprise a software interface for inputting commands, data or information or a screen or display for transmitting information to the user. The interface may allow the operator to input instructions to begin analysis for example, or to receive information about the determination of safe operation of the AES. Furthermore, the user may input an instruction to put the AES into a maintenance mode in which the high voltage output to the electrode is disengaged. This would allow maintenance tasks to be carried out to the electrode and spark stand, without risk of electrocution to the person doing the maintenance.

An atomic emission spectrometer (AES) may comprise the described controller. This AES may be safer to use because the controller imposes additional safety checks before analysis can begin (and during analysis). Furthermore, by implementing a technique to ascertain if the sample is correctly seated in the sample holder and spark stand, errors and anomalies in the sample analysis may be reduced.

In a second aspect there is described a method for establishing safe operation of an atomic emission spectrometer (AES) to analyse a sample arranged on a sample holder of the AES, the method comprising measuring an at least one test parameter indicative of the arrangement of the sample on the sample holder. The method further comprises comparing the at least one test parameter to a range of target values for the at least one test parameter to determine if the sample is arranged correctly on the sample holder. The method may use the determination of whether the sample is correctly seated to establish whether the AES is in a safe operating mode.

Preferably, the method comprises disabling an electrode of the AES if the at least one test parameter is not within the range of target values. Beneficially, the method prevents the electrode from being energised (i.e. prevents voltage being applied to the electrode) or can force a safety shut down of the electrode in the event that the sample is determined to be arranged incorrectly. In other words, the controller may place the electrode in an "OFF" state where characterisation of the sample indicates an unsafe mode of operation for the AES.

The at least one test parameter may be an electrical parameter dependent on a current between a first and second terminal at the sample holder. For example, in the correct arrangement, the sample may be positioned between the first and second terminal of the sample holder so that the sample is in electrical contact with both terminals. Advantageously, the measurement of an electrical parameter operates both as a check that a sample is present, and also whether the sample is correctly positioned. If the sample is not correctly positioned, good electrical contact will not be made between the sample and the terminals.

Optionally, the at least one test parameter is a gas pressure measured in a gas chamber housing an electrode of the AES. Advantageously, measurement of the gas pressure indicates whether a gas-tight seal has been formed between the sample and the sample receiver. If a gas-tight seal has not been formed, gas can leak from the chamber when the gas chamber is overpressured and the overpressure in the gas chamber cannot be maintained.

Alternatively, the at least one test parameter is a displacement of a portion of the sample holder. Beneficially, measurement of the displacement can take place during analysis of the sample. Displacement of a portion of the sample holder provides an indication that the sample has been moved. Therefore, measurement of the gas parameter can allow determination of a movement or adjustment of the sample during analysis, which is likely to indicate operation which is hazardous to the user of the AES.

Preferably, measuring the at least one test parameter as part of the method may comprise measuring each of two or more test parameters. Furthermore, comparing the at least one test parameter to a range of target values may comprise comparing each of the two or more test parameters to a range of target values for each test parameter. Advantageously, measuring two or more test parameters may provide additional characterisation of the arrangement of the sample on the sample holder. Therefore, the determination if the sample is arranged correctly on the sample holder may be more reliable.

Preferably, an electrode of the AES is disabled if one or more of the two or more test parameters is not within the range of target values for that test parameter. The electrode may be shut down safely or application of voltage to the electrode may be prevented. The electrode may be disabled if any one of a number of measured test parameters does not fall within the target range of values for that test parameter. Advantageously, this provides additional safety checks before hazardously high voltages are applied (or maintained) at the electrode.

Each of the two or more test parameters may be any one or more selected from the group consisting of: an electrical parameter dependent on a current between a first and a second terminal at the sample holder; a gas pressure in a gas chamber housing an electrode of the AES; and a displacement of a portion of the sample holder. Beneficially, each of the test parameters assesses different aspects of the sample set-up.

Optionally, the two or more test parameters are not the same test parameter. Advantageously, measuring more than one type of test parameter increases the accuracy of the determination whether the sample is properly arranged on the sample holder, as different aspects of the sample arrangement are considered and checked.

At least one of the two or more test parameters may be the electrical parameter. To measure the electrical parameter, the first terminal may be a sample receiver of the sample holder and the second terminal may be at a clamping element of the sample holder, the clamping element for securing the sample to the sample receiver. The electrical parameter may provide an indication of whether a sample is present at the sample holder, and moreover whether the sample is securely and correctly arranged so as to provide good electrical contact between the first and second terminal at the sample holder.

Prior to the measurement step, a current may be applied between the first terminal and the second terminal. The current may be sufficiently low that human contact with either of the terminals would not cause harm or injury. The current may be applied as a test current in order to measure the electrical parameter. As an alternative, a voltage could be applied between the first and second terminal.

Preferably, the electrical parameter is impedance. A known current, I, may be passed between the first and second terminals at the sample holder (and through the sample therebetween). Measurement of the voltage, U, between the first and second terminals can then be used to calculate the impedance, Z=U/I.

Preferably, at least one of the two or more test parameters is the gas pressure. Measurement of the gas pressure provides an indication whether the sample is correctly arranged on the sample holder such that a gas-tight seal is formed. If a gas-tight seal is not formed, an overpressure may not be created in the gas chamber.

The gas pressure may be measured after elapse of a time interval. The gas pressure may be measured after a predetermined time interval following initiation of a flow of gas though the gas chamber. Alternatively, the gas pressure may be measured as the change in gas pressure between a measurement at a first time and a measurement at a second time. Advantageously, the gas pressure may be measured after a predetermined time interval to establish whether a pressure greater that atmospheric pressure is present in the gas chamber.

Preferably, at least one of the two or more test parameters is the displacement. Beneficially, measurement of the displacement can take place during analysis of the sample. Measurement of displacement of a portion of the sample holder can indicate that the sample has been moved, and therefore that an error or accidental contact has occurred during analysis.

Optionally, the displacement is equal to a difference between a first position of a clamping element of the sample holder measured at a first time and a second position of the clamping element of the sample holder measured at a second time, the first and second position being measured relative to a sample receiver of the sample holder and the clamping element for securing the sample to the sample receiver. In a correct arrangement of the sample, the clamping element secures the sample to the sample receiver. Therefore movement or adjustment of the position of the clamping element may provide an indication that the sample has also been moved. Alternatively, the displacement may consider the change in position between a first time and a second time of another portion of the sample holder or the sample.

Optionally, the displacement comprises an angular displacement of the clamping element. The test parameter may instead comprise a measurement of a lateral displacement or other change in position of the clamping element or another portion of the sample holder or sample itself.

Preferably, preventing energising or disabling of an electrode comprises controlling a switch to regulate a high-voltage current through the electrode. The switch may comprise any type of circuit breaker, electrical conductor (for example to short-circuit a voltage to ground potential), or transistor. The switch may control a power supply connected to the electrode.

The method may be repeated at time intervals. The method may be repeated a number of times. For example, the method may be repeated before analysis of the sample is permitted to begin. The method may be repeated before and after analysis of the sample. In some cases, the method can be repeated one or more times during analysis of the sample.

A lamp may be illuminated when the electrode is energised. Advantageously, this provides a visual indication to the user of the AES that hazardously high voltages are in use at the equipment. Alternatively, a lamp may be illuminated when the method determines that a sample has been arranged correctly (or incorrectly) on the sample holder. The lamp may be useful as an additional safety feature.

In an example of a third aspect, there is a method for controlling a spark generator in a spark or atomic spectrometer (AES) having a sample holder comprising a sample receiver and a clamping element for securing a sample to the sample receiver. The method comprises: at a first time, measuring a first position of the clamping element; applying a current between a first and second terminal at the sample holder;

measuring an electrical parameter dependent on the voltage between the first and second terminal; measuring the gas pressure at a gas chamber of the AES;

comparing the electrical parameter to a range of target electrical parameter values;

comparing the gas pressure to a range of target gas pressure values; energising a power supply connected to an electrode if the electrical parameter is within the range of target electrical parameter values and the gas pressure is within the range of target gas pressure values; at a second time, measuring a second position of the clamping element; calculating the displacement of the clamping element by comparing the difference between the first position and the second position; comparing the displacement to a range of target displacement values; and, terminating energising of the electrode of the AES if the difference is not within the range of target displacement values. This sequence of steps may be particularly advantageous to determine whether the AES can be operated safely.

LIST OF FIGURES

The present invention will now be described, by way of example only, with reference to the accompanying drawings, in which.

In the drawings, like parts are denoted by like reference numerals. The drawings are not drawn to scale.

DETAILED DESCRIPTION

Figure 1:
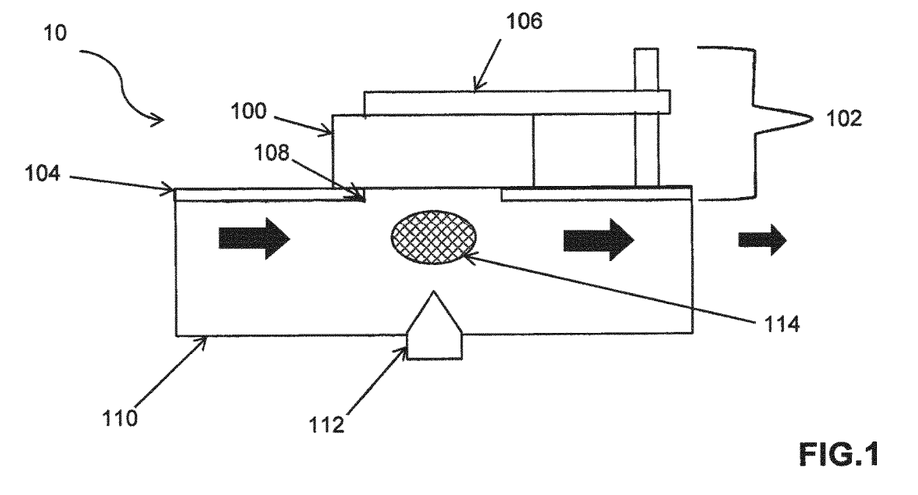
FIG. 1 is a side view of a spark stand of an atomic emission spectrometer (AES)
Figure 2:
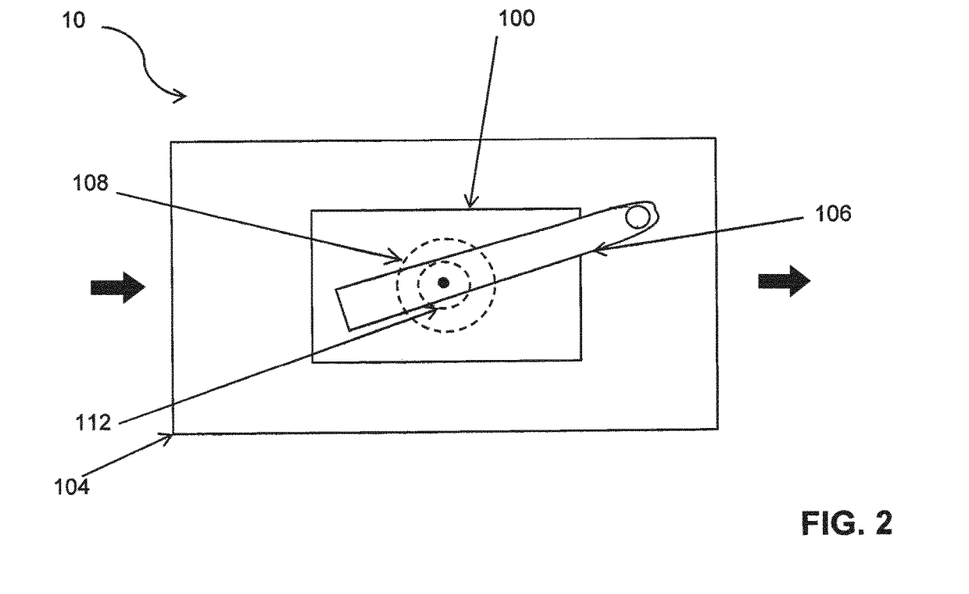
FIG. 2 is a plan view of the spark stand of FIG. 1.

A spark stand or spark table 10 of an AES is represented in a side view in FIG. 1, with the same spark stand 10 being shown as a plan view in FIG. 2. The sample holder 102 of the spark stand 10 comprises a sample receiver or analysis table 104 and a clamping element or clamp arm 106. The analysis table 104 is held at a fixed voltage, normally a ground potential. A sample 100 is arranged within the sample holder 102, by placement on the sample receiver 104 and securing by the clamping element 106. The clamping element 106 applies a force to the sample 100 to ensure that the sample cannot move and is pressed down onto the sample receiver 104.

The sample receiver 104 comprises an aperture 108. The aperture or hole 108 provides an opening directly into a gas chamber 110. The gas chamber 110 has an input and output (not shown) to allow a gas to flow through the gas chamber 110 (as denoted by the arrows in FIGS. 1 and 2). When the sample 100 is securely and correctly arranged on the sample receiver 104 using the clamping element 106, the aperture 108 is sealed by the sample 100. In other words the clamping element 106 presses the sample 100 onto the sample receiver 104 to form a gas-tight seal between the sample 100 and the sample receiver 104.

Within the gas chamber 110 and directly adjacent to the aperture 108 in the sample receiver 104 is an electrode 112. The electrode 112 is suitable for carrying a high voltage. The electrode 112 is arranged close to, but spaced apart from, the sample receiver 104 (and the sample 100, when in place).

In use, a gas flows through the gas chamber 110 between the input and the output to the chamber 110. When the sample 100 is in the correct arrangement, the gas cannot leak from the aperture 108 at the sample receiver 104, due to the seal formed with the sample 100. In this example, the gas is an inert gas such as argon.

To begin analysis of the sample 100, a high-voltage is applied to the electrode 112 by a power supply (not shown). As a consequence, a spark or arc is formed between the high potential electrode 112 and the sample receiver 104 (which is held at a much lower potential, normally a ground potential). The spark or arc causes ablation or vaporisation of a portion of the sample 100 which is exposed to the arc through the aperture 108. The vaporised sample results in a plasma 114. Light emission from the plasma 114 passes from the gas chamber 110 towards a spectrometer (not shown) for optical analysis.

The electrode power supply (or spark generator) may be a combination of a high-current-controlled source (CCS) and a high-voltage power supply (an ignitor). Each spark generated at the electrode may be a combination of a high-voltage discharge between the electrode and the sample and an application-specific current shape flowing through the electrode, the ionisation channel, the sample and finally the sample receiver or analysis table.

The present invention looks to improve the safety of the AES by measurement of various test parameters. The test parameters are compared to preferred or target values for the given test parameter. If the test parameter is outside the preferred or threshold values, this indicates the sample 100 is not correctly seated on the sample holder 102. If this is the case, use of the electrode 112 is prevented because application of a high voltage to the electrode 112 when the sample is incorrectly seated may be unsafe for the user of the AES.

The invention aims to fulfil the safety requirements for electrical equipment for measurement, control and laboratory use (according to harmonised international standard IEC 61010-1:2010). Furthermore, the AES having a controller according to the present invention aims to comply with the Low Voltage Directive 2006/95/CE, which is a requirement to obtain a "CE" mark in the European Union. Certain terminology is considered and defined in IEC 61010-1:2010, including a definition of accessible parts (section 6.2), hazardous voltage (section 6.3), normal use (section 3.5.8), single fault condition (section 3.5.10) and reasonably foreseeable misuse (section 16.1).

Figure 3:
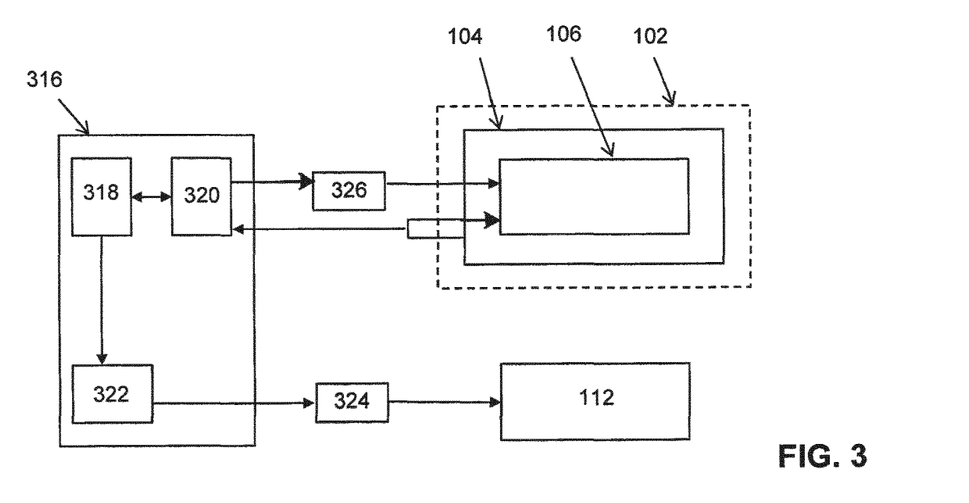
FIG. 3 is a schematic view of the controller according to one example.

FIG. 3 illustrates the measurement of a first test parameter. In this example, the test parameter is an electrical characteristic. The electrical characteristic is dependent on the current passing between two terminals at the sample holder 102.

FIG. 3 shows a controller 316, having a control module 318, a measurement module 320 and an electrode disabling module 322. The control module 318 is configured to communicate with the measurement module 320 and electrode disabling module 322. FIG. 3 further shows the sample holder 102, comprising a first terminal at the sample receiver 104 and a second terminal at the clamping element 106. FIG. 3 further shows the electrode 112. The electrode 112 is configured to be controlled by the electrode disabling module 322 at the controller 316 via a power supply 324. The power supply 324 is a high-voltage/high-current power supply.

In use, the control module 318 of the controller 316 initiates the measurement module 320 to apply a current between the two terminals at the sample holder 102. In particular, a current is applied by a secondary power supply 326 to the clamping element 106. The sample receiver 104 is held at a ground potential. The voltage between the clamping element 106 and sample receiver 104 of the sample holder 102 is then measured by the measurement module 320 of the controller 316.

The controller 316 calculates at the measurement module 320 the impedance between the two terminals of the sample holder 102. The measurement module 320 compares the measured impedance to a range of target impedance values stored at by the measurement module 320. A status indicator is sent to the control module 318, which indicates whether the measured impedance falls within the range of the target impedance.

The control module 318 determines if the sample 100 is correctly positioned on the sample receiver 104 according to the received status indicator. In this example, if the electrical impedance is in a range less than 100 mΩ, this indicates the sample 100 is correctly positioned on the sample receiver 104. Where the control module 318 determines the sample 100 is correctly arranged on the sample receiver 104, the control module 318 communicates with the electrode disabling module 322 to allow the electrode to be energised 112. In this example, the electrode disabling module 322 controls a switch to activate the high-voltage/high-current power supply 324. The power supply 324 provides a high-current to the electrode 112, resulting in the required high voltage between the electrode 112 and sample receiver 104 to generate a spark.

Alternatively, in this example if the electrical impedance is determined to be greater than 100 mΩ (i.e. outside of the range of target values for the test parameter), the control module determines that the sample 100 is not correctly positioned on the sample receiver 104. Therefore, the control module 318 passes an instruction to the electrode disabling module 322 to prevent energising of the electrode 112. In particular, the electrode disabling module 322 controls a switch to prevent the power supply 324 from applying a voltage to the electrode 112.

In this example, the measurement of the electrical impedance takes place before analysis of the sample 100 begins. Therefore, the controller 316 prevents the power supply 324 from applying any voltage to the electrode 112. However, in other examples, the controller 316 may be configured to stop or abort the application of a voltage to the electrode 112 once analysis has begun.

Although reasonably foreseeable misuse of the AES cannot be ruled out using the described method, in this example the operational safety is improved because measurement of the electrical parameter guarantees the operator's safety when in normal use or when the apparatus is operating under single fault condition. This approach is compatible with the requirements of the IEC 61010-1:2010 harmonised standard.

Figure 4:
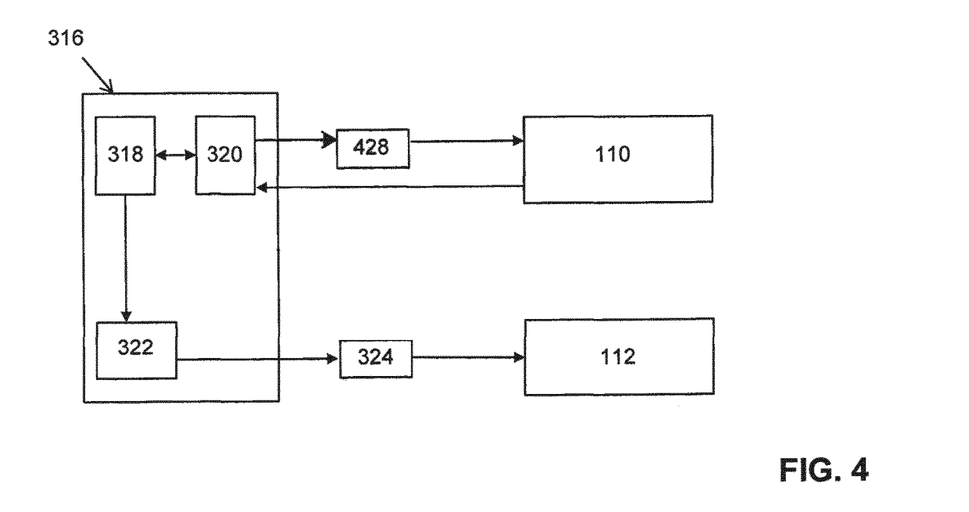
FIG. 4 is a schematic view of the controller according to a further example.

FIG. 4 illustrates a configuration of apparatus for measurement of a second test parameter. In this configuration, the test parameter is a gas pressure within the gas chamber 110. In FIG. 4, the controller 316 comprises a control module 318 in communication with a measurement module 320 and an electrode disabling module 322. FIG. 4 further shows the gas chamber 110 and the electrode 112 of the spark stand 10 of the AES. A gas controller 428 controls the flow of gas (in this example, argon gas) through the gas chamber 110. The electrode 112 is configured to be controlled by the electrode disabling module 322 at the controller 316 via a power supply 324. The power supply 324 is a high-voltage/high-current power supply.

In use, the controller 316 communicates with the gas controller 428 to initiate a flow of argon gas through the gas chamber 110. The gas controller 428 applies an adequate flow of gas to cause an overpressure at the gas chamber 110 (in other words, a pressure greater than atmospheric pressure). Where the sample 100 is correctly arranged in the sample receiver 104 and the aperture 108 in the sample receiver 104 is completely sealed by the sample 100, an overpressure in the gas chamber 110 should be achieved within a predetermined time period. After this time period has elapsed, the measurement module 320 at the controller 316 measures the pressure within the gas chamber 110 (e.g. by means of a pressure gauge or sensor (not shown). For example, the pressure sensor may be an absolute pressure sensor integrated circuit at the controller 316. If the measured gas pressure is greater than a threshold gas pressure, it is determined that the sample 100 is correctly arranged such that a seal has been formed between the sample 100 and the sample receiver 104. A status indicator is sent to the control module 318 to indicate that the measured gas pressure is within the target range of values (i.e. that it has exceeded the threshold value).

Upon receiving a positive status indicator (i.e. that the measured gas pressure is within the range of target values) the control module 318 communicates with the electrode disabling module 322 to allow energising of the electrode 112. Upon receipt of this instruction, the electrode disabling module 322 may activate a switch to permit the power supply 324 to apply a voltage to the electrode 112 of the spark stand 10. In some cases, the current may be immediately applied upon activation of the switch, although in other cases the current will only be applied upon receipt of further instruction from the operator (for example, via a human-machine interface).

If, upon performing the measurement according to FIG. 4 the sample 100 has not been correctly arranged on the sample receiver 104, it is likely that a proper seal between the sample 100 and sample receiver 104 will not be formed. For example, this may be because the sample has not been properly mounted on the sample holder, or that the sample is not correctly sized to cover the aperture at the sample receiver. If this is the case, gas will leak from the gas chamber 110 when the gas controller 428 attempts to create an overpressure in the gas chamber 110. Leakage from the gas chamber 110 means that an overpressure will not be achieved within the predetermined time period. According to the present example, in this case measurement by the measurement module 320 of the gas pressure in the gas chamber 110 after the predetermined time period would give a gas pressure below the threshold or target gas pressure.

Upon comparison of the measured gas pressure with the target gas pressure range by the measurement module 320, it is determined that the sample 100 is incorrectly arranged and an associated status indicator is sent to the control module 318.

On receipt of this (negative) status indicator the control module 318 sends a communication to the electrode disabling module 322 to prevent energising of the electrode 112 of the spark stand 10. In this example, this causes the electrode disabling module 322 to activate a switch to prevent initiation of the power supply 324 and to avoid application of voltage to the electrode 112.

Beneficially, by verifying that a gas-tight seal has been formed between the sample 100 and the sample receiver 104, it is deduced that the aperture 108 in the sample receiver 104 is entirely covered. Therefore, the electrode 112 (housed within the gas chamber 110) cannot be exposed to the operator whilst the sample 100 is correctly in place. Therefore, the measurement of the gas parameter mitigates some of the risks of operation of the AES, in particular risk due to reasonably foreseeable misuse.

Figure 5:
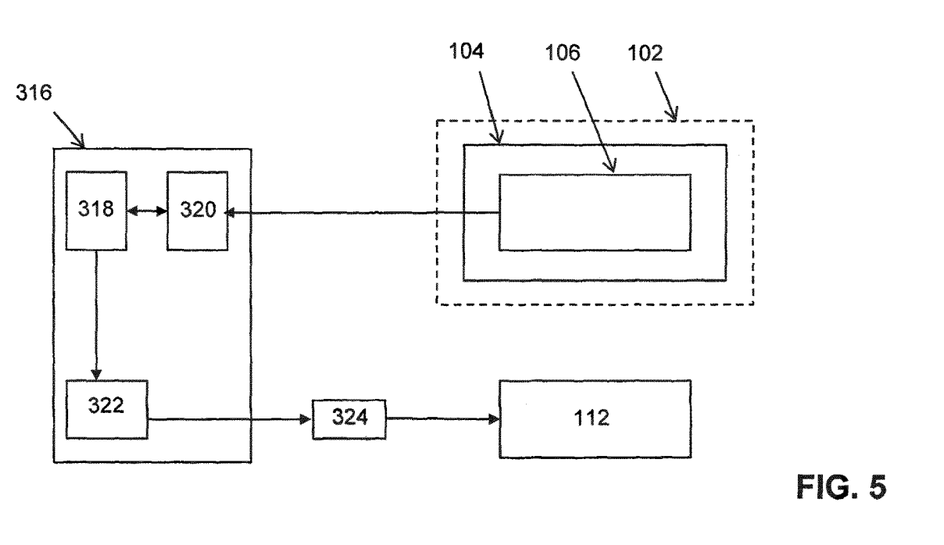
FIG. 5 is a schematic view of the controller according to another example.

FIG. 5 illustrates a configuration of apparatus for measurement of a third test parameter to indicate whether the AES is correctly configured for safe operation. In this example, the test parameter is the displacement of a portion of the sample holder 102. In particular, the test parameter is the angular displacement of the clamping element 106 of the sample holder 102.

In this example, the controller 316 comprises a control module 318, a measurement module 320, and an electrode disabling module 322. The measurement module 320 is arranged to measure a position of a portion of the sample holder 102, specifically the position of the clamping element 106, e.g. by means of a position encoder. The electrode disabling module 322 is in communication with a high-power, high-voltage power supply 324 which is connected to the electrode 112 at the spark stand 10.

In this example, the displacement is measured by means of an optical, absolute incremental encoder at the base of the shaft of the clamping element 106. This allows any movement of the clamping element 106 with respect to the axis of the shaft to be detected by the encoder. In particular, the encoder measures an angular displacement of the clamping element 106.

In use, a position of the clamping element 106 is measured by the measurement module 320 at a first time. The position of the clamping element 106 can be measured with respect to a fixed portion of the sample holder 102, such as the sample receiver 104. At a second time (a predetermined time interval from the first time) the position of the clamping element 106 is measured again by the measurement module 320 of the controller 316. The measurement module 320 determines a displacement of the clamping element 106 by calculating the difference between the position measured at the first time and the position measured at the second time. Where a non-zero displacement is calculated, this indicates the sample 100 has been moved.

The measurement module 320 compares the calculated displacement to a target or threshold value. In this example, the target value for the displacement is zero, although a small range of target values may be appropriate in some alternative examples to allow for error in the position measurement (for example, an angular displacement of the clamping element to within ±1°). The measurement module 320 provides a status to the control module 318 of the controller 316 to indicate whether the displacement is equal to the target value. In the event that the status indicates that the displacement is outside of the target value (e.g. non-zero), the control module 318 instructs the electrode disabling module 322 to disable the electrode 112 by initiating a switch at the power supply 324. Where a voltage is already applied by the power supply 324 to the electrode 112, initiation of the switch safely dissipates the associated high voltage. If a voltage has not yet been applied to the electrode 112, the electrode disabling module 322 prevents the power supply 324 from applying a voltage to the electrode 112.

If, upon measurement of the displacement by the measurement module 320 the displacement is determined to be zero (within any bunds of error), the measurement module 320 notifies a positive status indicator to the control module 318. In this case, the controller 316, via the electrode disabling module 322, allows initiation of a high voltage at the electrode 112.

In the described example, the first measurement at a first time takes place before analysis of the sample 100 has begun (and so before any voltage is applied to the electrode 112). The second measurement at a second time takes place a short time after the analysis has begun and the voltage has been applied to the electrode 112. If any difference between the two positions is measured, this indicates the sample 100 has been moved during the analysis. In some circumstances this is due to contact with the operator and so it is important that the electrode 112 is disabled as quickly as possible to prevent harm to the operator.

In this example, the displacement of the clamping element 106 is measured repeatedly throughout analysis of the sample 100 (and throughout the period during which hazardous voltages may be present at the spark stand 10). The measurement module 320 calculates the displacement of the clamping measurement compared to any previous measurement. If at any time, the clamping element 106 is determined to have been moved, the electrode 112 and/or power supply 324 is disabled by the electrode disabling module 322.

In an alternative example, before commencement of the sample analysis the configuration of FIG. 5 can measure an absolute position of the clamping element 106 of the sample holder 102 relative to a fixed portion of the sample holder 102, such as the sample receiver 104. By comparison of this absolute position relative to a range of desired positions, it can be determined if the clamping element 106 is arranged in the ideal position for analysis of the sample 100.

In a particularly advantageous example, more than one of the test parameters can be measured to provide a determination if the sample 100 is correctly arranged. Each of the test parameters characterise different aspects of the sample arrangement. Therefore, measuring a combination of the test parameters (together with subsequent comparison to the target values for that test parameter) gives an enhanced and more reliable indication whether operation of the apparatus would be safe.

Any combination of the described test parameters may provide a useful indicator if the sample 100 is correctly arranged. For example, measurement of an electrical parameter such as impedance (a described above) could be made in combination with measurement of the gas pressure in the gas chamber 110. In an alternative example, the gas pressure could be measured in combination with the displacement of a portion of the sample holder 102 (or other indicator of displacement of the sample 100). In a still further example, an electrical parameter and the displacement could both be measured.

Figure 6:
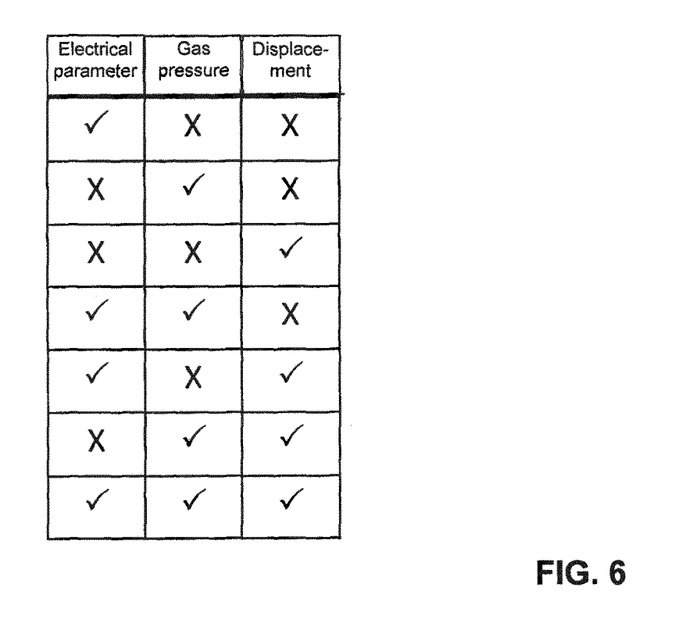
FIG. 6 is a table showing possible combinations of test parameters.

Possible combinations of the one or more test parameters to be measured are shown in FIG. 6. Where more than one test parameter is measured, each test parameter is compared to a range of target values for that particular test parameter. In the event that the one or more test parameters do not fall within the target range of values, the controller 316 prevents a voltage being applied to the electrode 112 of the spark stand 10, or otherwise disables the electrode 112. By this method, the various aspects of the sample positioning are checked and used to determine if the sample 100 is positioned correctly for safe operation.

In one example, an electrical parameter and the gas pressure can be measured. Advantageously, measurement of the electrical parameter (for example, the impedance) indicates whether the sample has been correctly mounted so as to give good electrical contact to the sample receiver (and so causing the sample to be held at the ground potential). In conjunction with measurement of the electrical parameter, measurement of the gas pressure verifies that the gas chamber is gas-tight during the course of an analysis. This indicates that the aperture in the sample receiver is completely covered by the sample, and so the electrode cannot be exposed to the operator. Therefore, the combination of the measurement of these two test parameters mitigates some of the risks due to reasonably foreseeable misuse of the AES.

It is particularly beneficial if all three described measurement parameters are measured and compared. This provides an especially reliable method of indicating safe operation. The additional measurements provide further parameters to identify hazardous or improper use of the AES. As each test parameter considers different characteristics of the set-up, measuring all three test parameters increases the accuracy of the risk assessment performed by the method, which must be passed before voltage is permitted to be applied to the electrode of the AES. Each of the proposed measurements contributes to an overall improvement in the operational safety of the AES. Measurement of each safety parameter serves a particular purpose and characterises a different aspect of the sample set-up.

Figure 7:
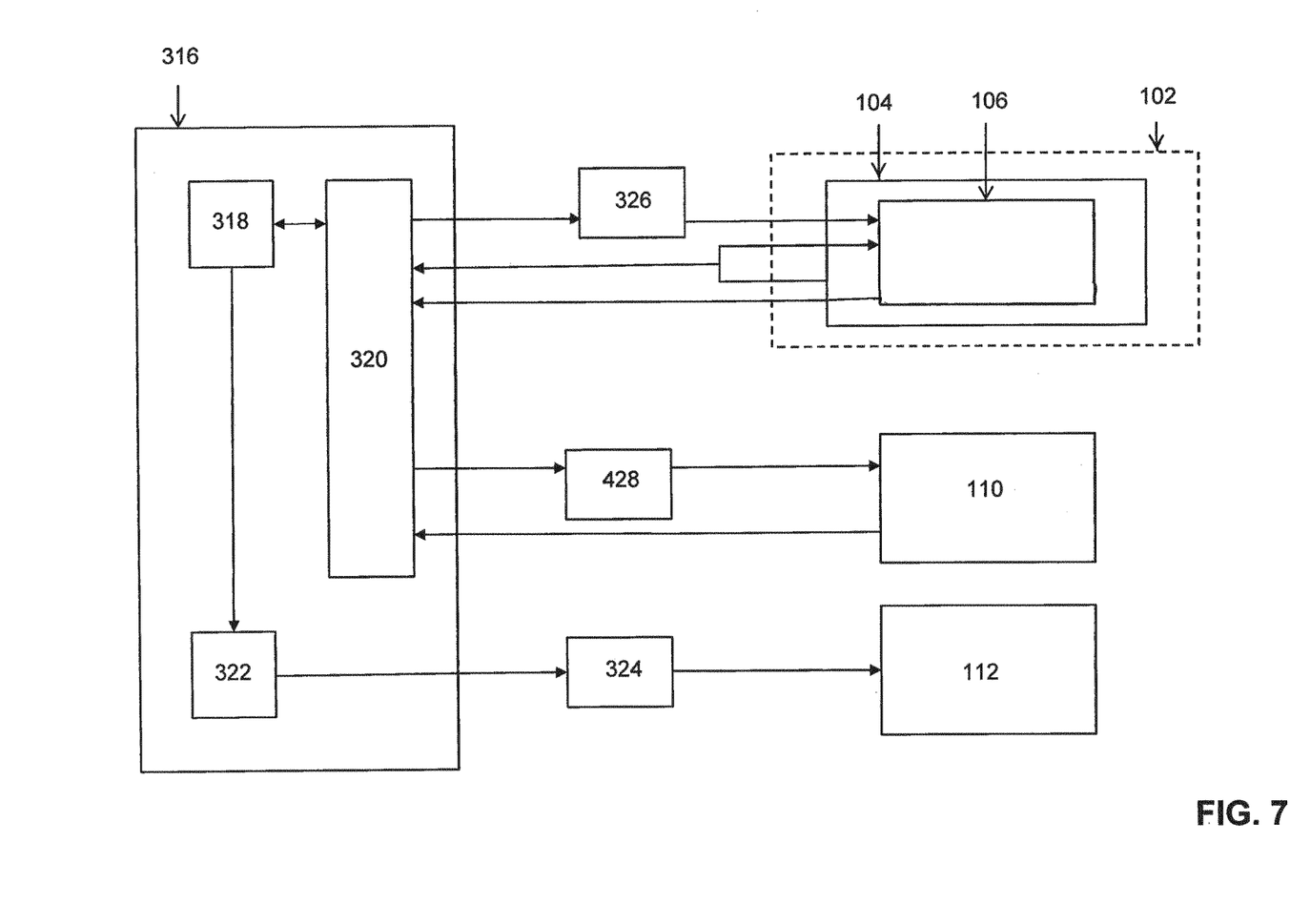
FIG. 7 is a schematic view of the controller according to a still further example.

FIG. 7 illustrates apparatus for measurement of all three described test parameters. FIG. 7 shows a controller 316 having a control module 318 and a measurement module 320. The controller 316 further comprises an electrode disabling module 322. Components of the spark stand 10 shown include the sample receiver 104, the clamping element 106, the gas chamber 110 and the electrode 112. A current may be applied to the clamping element 106 via a secondary power supply 326. A high-voltage, high-current power supply 324 is provided to supply a voltage to the electrode 112. A gas controller 428 can be used to control the flow of gas to the gas chamber 110.

Before the AES begins analysis, the operator will first place the sample 100 on the sample receiver 104 and secure the sample in position over the aperture 108 or opening to the gas chamber 110 using the clamping element 106. The operator may then initiate the analysis of the sample 100 via an instruction at the controller 316.

In use, the controller 316 instructs the measurement module 320 to apply a low current to a first terminal of the sample holder 102 using a secondary power supply 326. In this example, the first terminal of the sample holder 102 is the clamping element 106. Subsequently, the measurement module 320 measures the voltage between the clamping element 106 and a second terminal of the sample holder 102 at the sample receiver 104. The measurement module 320 calculates the impedance between the first and second terminal of the sample holder 102 and compares the measured impedance to a range of target values for the parameter. Based on the result of the comparison, the measurement module 320 passes a status indicator to the control module to indicate whether or not the electrical impedance is within the given range of target values.

Simultaneously with or subsequent to the measurement and comparison of the impedance test parameter, the measurement module 320 obtains a measurement of the gas pressure in the gas chamber 110. First, the measurement module 320 instructs the gas controller 428 to begin a flow of gas though the gas chamber 110. The gas flow is sufficient to create an overpressure if the gas chamber 110 is sealed. After a predetermined time interval, the measurement module 320 receives or obtains a measurement of the gas pressure within the gas chamber 110. The measurement module 320 compares the measured gas pressure to a range of target values for the gas pressure. In this example, the target values for the gas pressure are values greater than a threshold value. Upon comparison of the measured gas pressure with the range of target values, the measurement module 320 provides a status indicator to the control module 318 to designate whether the measured value is within the range of target values.

A third test parameter is also measured upon initiation of a sample analysis by the operator of the AES. The controller 316, via the measurement module 320, acquires a first measurement of the position of the clamping element 106 of the sample holder 102. After a short time interval (for example, a few seconds), the measurement module 320 acquires a second measurement of the clamping element 106. The measurement module 320 then calculates the difference between the two position measurements to give the displacement of the clamping element 106 during the time interval.

The measurement module 320 compares the displacement of the clamping element 106 to a range of target values. In this case, the target value for the displacement is zero within the bounds of error for the measurement. If a non-zero displacement of the clamping element 106 is detected, this indicates the sample 100 has been moved. After the comparison of the measured displacement to the target values for the displacement, the measurement module 320 provides a status indicator to the control module 318 which represent the result of the comparison (i.e. whether the measured value is within the target range).

The described measurement of the displacement may be repeated successively. Advantageously, the measurements are repeated throughout the analysis of the sample 100 (and in particular, throughout the time when a hazardous voltage is applied to the electrode 112 of the AES). Each measurement may be taken following a predetermined time interval and the difference between the new position measurement and the previous measurement (or average of the previous measurements) is calculated by the measurement module 320. In each case, the displacement is compared to a target range of values and a status indicator representative of the outcome of the comparison is sent to the control module 318.

As described above, measurement and comparison of each of the three test parameters yields a status indicator at the control module 318. Upon receipt of the status indicators, the control module 318 determines if, according to those indicators, the sample 100 is incorrectly positioned on the sample holder 102. If the sample 100 is determined to be incorrectly positioned, the control module 318 sends an instruction to the electrode disabling module 322 to disable the electrode 112, for example by the power supply 324 in an "OFF" state. If the electrode 112 already has a high-voltage current applied (for example, if analysis has already begun), the electrode disabling module powers off the power supply 324 and grounds any potential at the electrode 112. The sample analysis is aborted.

Alternatively, if the control module determines that all status indicators received from the measurement module 320 indicate a safe arrangement of the sample 100 on the sample holder 102, the control module instructs the electrode disabling module 322 to permit the electrode 112 to be energised, or to continue to be energised. Therefore, vaporisation of the sample may take place and the sample full analysis is performed.

Figure 8:
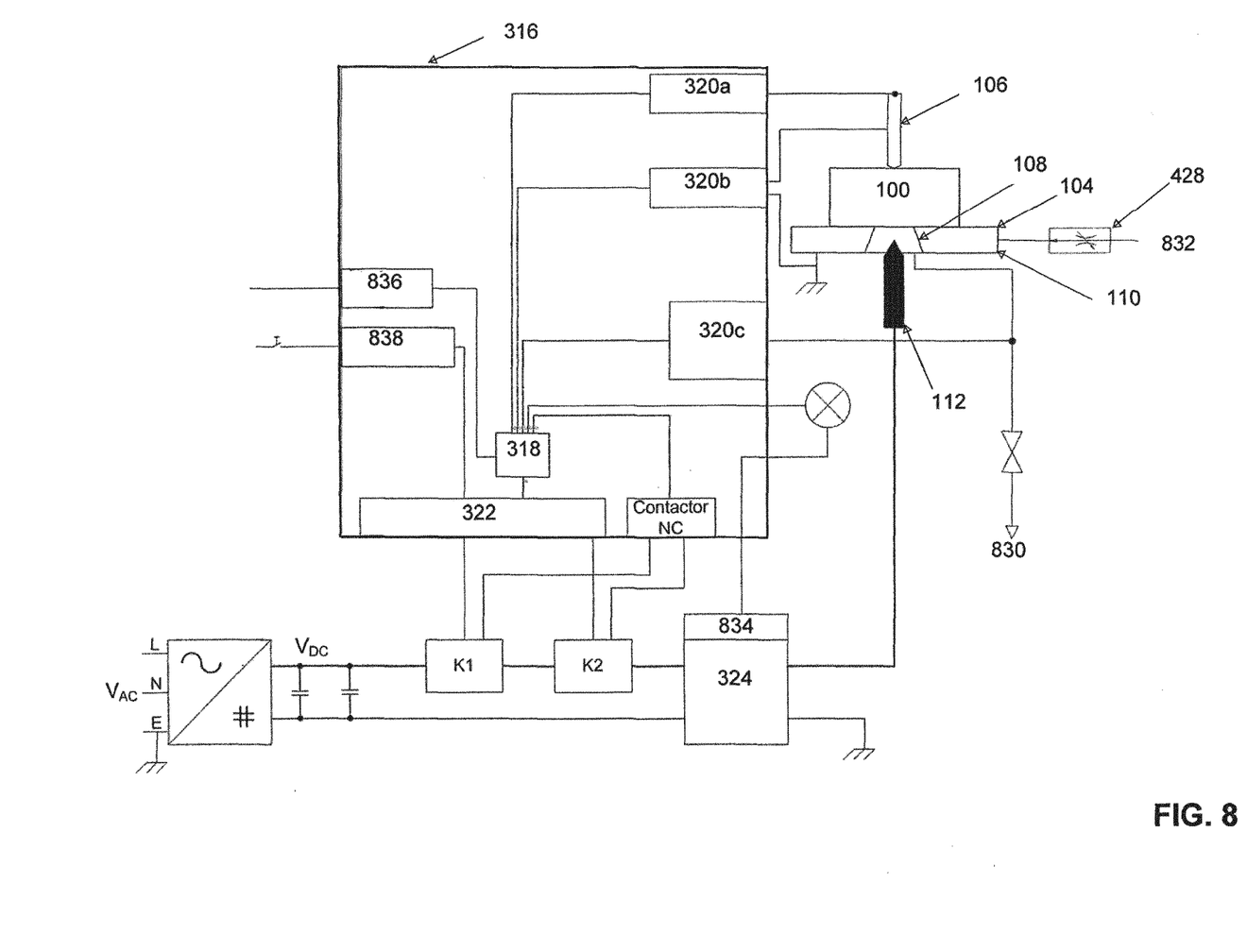
FIG. 8 is a diagram showing the configuration of apparatus for implementation of the controller of FIG. 7.

FIG. 8 shows a circuit diagram for a particular implementation of the control system described above in relation to FIG. 7. In FIG. 8, the spark stand is shown having the sample receiver 104 with an aperture 108, a clamping element 106 and an electrode 112. The sample 100 is arranged on the spark stand. A flow of argon gas from argon input 832 into the gas chamber 110 is controlled by gas controller 428. The gas exits the gas chamber through argon output 830.

The electrode is connected to electrode power supply 324, together with lamp 834. In use, the lamp is illuminated when the electrode power supply 324 is in an "ON" state. As such, the lamp acts as a visual warning to the operator of the AES that hazardously high voltage is present.

FIG. 8 further comprises a controller 316, which operates as described above with reference to FIG. 7. The controller comprises a control module 318, an electrode disabling module or high voltage control 322, and measurement modules 320a, 320b, 320c for measurement of each test parameter. In FIG. 8, measurement module 320a measures the displacement of clamping element 106, measurement module 320b measures the electrical impedance between the clamping element 106 and the sample receiver 104 (i.e. through sample 100) and measurement module 320c measures the gas pressure. The controller of FIG. 8 also comprises a user interface 836, which may be any type of human machine interface including, for example, a keyboard, screen, a touch screen or a mouse. Mechanical switch 838 can be used to manually disable the power supply to the electrode.

Figure 9:
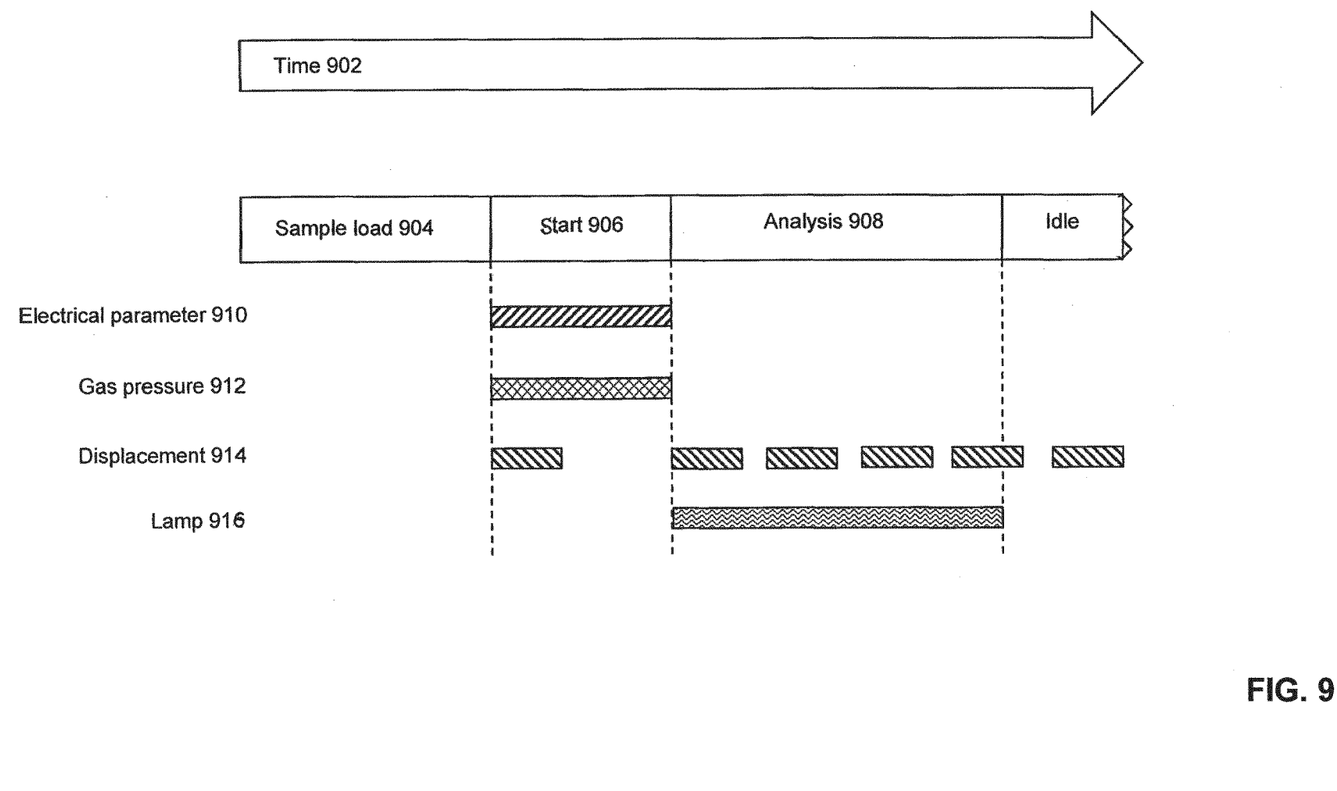
FIG. 9 is a schematic view of sequence of measurements in a particular example.

FIG. 9 shows a representation of the sequence of measurements performed by the controller and apparatus discussed above in relation to FIGS. 7 and 8. FIG. 9 represents the measurements as a sequence in time 902. In a first period (the idle or sample loading period 904) the operator loads a sample 100 onto the sample receiver 104. During this time period, the operator may be in contact with the sample holder 102, and so high voltages must not be permitted at the electrode 112. Therefore, during this time period the electrode disabling module 322 of the controller 316 prevents the electrode 112 from being energised, for example by control of a switch to the high-current/high voltage power supply 324.

Once the operator has loaded the sample 100, they will initiate analysis of the sample by the AES. This instruction may be made via a human-machine interface 836 for the controller 316, for example. After analysis is initiated, the controller 316 undertakes the automated method to determine if the sample 100 is correctly arranged for safe operation.

In a start-up time period 906, measurements are made of all three test parameters (the electrical parameter 910, the gas pressure 912, and the displacement 914). During this time period, the electrode disabling module 322 prevents application of any voltage to the electrode 112.

The gas pressure 912 is measured a predetermined time after commencement of the flow of gas into the gas chamber 110 by the gas controller 428, so as to allow time for an over pressure to occur or build up. However, the gas pressure is still measured during the start-up time period.

After measurement of each of the test parameters, the electrical test parameter 910 and gas pressure 912 are compared to their respective target values. A determination is made whether the measured values are within the target values. If so, the controller 316 allows analysis of the sample 100 to begin, as described below. If the measured values are determined not to be within the target range of values, the controller 316 prevents any voltage from being applied to the electrode 112, and disables the electrode 112. The analysis is aborted and the controller 316 provides a notification of this to the operator of the AES. This could be via illumination of an indicator lamp or via a message at the human-machine user interface 836 for the AES.

If, after the start-up period 906 the controller 316 determines the electrical parameter 910 and gas pressure 912 fall within their required target values, the analysis time period 908 will begin. The controller 316 instructs the electrode disabling module 322 to permit or initiate a high-voltage to be applied to the electrode 112 by the high-voltage/high current power supply 324. This creates a spark or arc between the electrode 112 and sample holder 102, as described above. Moreover, this causes ablation of a portion of the sample 100, upon which optical analysis can proceed.

During the analysis time period 908, the controller 316 obtains successive measurements of the position of the clamping element 106. For example, a new measurement may be taken every second, or every 3 seconds. Upon receipt of each measurement, the controller 316 calculates the displacement 914 of clamping element 106, being the difference between the new position measurement and at least one earlier position measurements. The controller 316 compares each newly calculated displacement 914 with a range of target values. Whilst the measured displacement 914 remains within the target range of values, the controller 316 allows the analysis to proceed and a voltage to be applied to the electrode 112.

If at any time during the analysis time period 908 a calculated displacement 914 is found to be non-zero, this is an indication that the clamping element 106 (and so sample 100) has been moved (for example, due to an accidental or inadvertent touch by the operator). Where a non-zero displacement is detected, the controller 316 immediately instructs the electrode 112 to be disabled. In other words, the power supply 324 is switched off, and any voltage on the electrode 112 is grounded.

A lamp 916 is illuminated when high-voltage is present on the electrode 112. For example, the lamp 916 is lit throughout the analysis time period.

Many combinations, modifications, or alterations to the features of the above embodiments will be readily apparent to the skilled person and are intended to form part of the invention. Any of the features described specifically relating to one embodiment or example may be used in any other embodiment by making the appropriate changes.

For example, a mechanical switch may be included at the spark stand 10 or as part of the controller 316. The purpose of the switch is to force the control module 318 at the controller 316 to open the high-voltage current path to the electrode 112 (or to ground the high-voltage). The mechanical switch is for use by the operator, and can be used to disable the electrode 112 during maintenance related tasks when the spark stand 10 is open and there is increased likelihood of exposure to the electrode. The operator's operational safety is further improved by addition of the mechanical switch.

It is noted that in each of the examples described with respect to FIGS. 3, 4, 5, 7 and 8, the comparison of the measured test parameter with a target range of values or threshold value takes place at the measurement module of the controller. However, equally the comparison could take place at the control module, or another element of the controller. Furthermore, although the description mentions the controller comprising individual modules or units, the controller may instead comprise a single entity. The controller may provide all forms of functionality described in relation to the individual modules, without any specific functionality being attributed to separate modules.

The invention claimed is:

1. A controller for establishing safe operation of an atomic emission spectrometer (AES) to analyse a sample arranged on a sample holder of the AES, the controller configured to:
   receive a measurement of each of two or more test parameters indicative of the arrangement of the sample on the sample holder; and
   compare each of the two or more test parameters to a range of target values for each test parameter to determine if the sample is arranged correctly on the sample holder.

2. The controller according to claim 1, the controller further configured to disable an electrode of the AES if one or more of the two or more test parameters is not within the range of target values for that test parameter.

3. The controller according to claim 1, wherein each of the two or more test parameters is selected from the group consisting of:
   an electrical parameter dependent on the current between a first and a second terminal at the sample holder;
   a gas pressure in a gas chamber housing an electrode of the AES;
   a displacement of a portion of the sample holder.

4. The controller according to claim 1, wherein the two or more test parameters are not the same test parameter.

5. The controller according to claim 3, wherein at least one of the two or more test parameters is the electrical parameter.

6. The controller according to claim 5, wherein the first terminal is at a sample receiver of the sample holder and the second terminal is at a clamping element of the sample holder, the clamping element for securing the sample to a sample receiver of the sample holder.

7. The controller according to claim 5, wherein the controller is further configured to initiate a current between the first terminal and the second terminal.

8. The controller according to claim 5, wherein the electrical parameter is impedance.

9. The controller according to claim 3, wherein at least one of the two or more test parameters is the gas pressure.

10. The controller according to claim 9, wherein the gas pressure is measured after elapse of a time interval.

11. The controller according to claim 3, wherein at least one of the two or more test parameters is the displacement.

12. The controller according to claim 11, wherein the displacement is equal to a difference between a first position of a clamping element of the sample holder measured at a first time and a second position of the clamping element of the sample holder measured at a second time, the clamping element for securing the sample to the sample receiver.

13. The controller according to claim 11, wherein the displacement is an angular displacement of the clamping element.

14. The controller according to claim 2 wherein disabling the electrode comprises controlling a switch to regulate a high-voltage current through the electrode.

15. The controller according to claim 1, further configured to provide a visual indicator when the electrode is energised.

16. An atomic emission spectrometer (AES) comprising the controller according to claim 1.

17. A method for establishing safe operation of an atomic emission spectrometer (AES) to analyse a sample arranged on a sample holder of the AES, comprising:
 measuring each of two or more test parameters indicative of the arrangement of the sample on the sample holder; and
 comparing each of the two or more test parameters to a range of target values for each test parameter to determine if the sample is arranged correctly on the sample holder.

18. The method according to claim 17, further comprising disabling an electrode of the AES if one or more of the two or more test parameters is not within the range of target values for that test parameter.

19. The method according to claim 17, wherein each of the two or more test parameters is selected from the group consisting of:
 an electrical parameter dependent on a current between a first and a second terminal at the sample holder;
 a gas pressure in a gas chamber housing an electrode of the AES;
 a displacement of a portion of the sample holder.

20. The method according to claim 17, wherein the two or more test parameters are not the same test parameter.

21. The method according to claim 19, wherein at least one of the two or more test parameters is the electrical parameter.

22. The method according to claim 21, wherein the first terminal is a sample receiver of the sample holder and the second terminal is at a clamping element of the sample holder, the clamping element for securing the sample to the sample receiver.

23. The method according to claim 21, further comprising prior to the measurement step, applying a current between the first terminal and the second terminal.

24. The method according to claim 21, wherein the electrical parameter is impedance.

25. The method according to claim 19 wherein at least one of the two or more test parameters is the gas pressure.

26. The method according to claim 25 wherein the gas pressure is measured after elapse of a time interval.

27. The method according to claim 19, wherein at least one of the two or more test parameters is the displacement.

28. The method according to claim 27, wherein the displacement is equal to a difference between a first position of a clamping element of the sample holder measured at a first time and a second position of the clamping element of the sample holder measured at a second time, the first and second position being measured relative to a sample receiver of the sample holder and the clamping element for securing the sample to the sample receiver.

29. The method according to claim 27, wherein the displacement is an angular displacement of the clamping element.

30. The method according to claim 18 wherein disabling of an electrode comprises controlling a switch to regulate a high-voltage current through the electrode.

31. The method according to claim 17, wherein the method is repeated at time intervals.

32. The method according to claim 17, further comprising the step of illuminating a lamp when the electrode is energised.

* * * * *